US010921965B1

(12) United States Patent
Goodwin et al.

(10) Patent No.: US 10,921,965 B1
(45) Date of Patent: Feb. 16, 2021

(54) COMPUTING SYSTEM FOR PRESENTING PATIENT HEALTH RECORDS IN A PROBLEM-CENTRIC MANNER

(71) Applicant: Allscripts Software, LLC, Raleigh, NC (US)

(72) Inventors: Joshua Goodwin, Old Hickory, TN (US); Tyrale Bloomfield, Nolensville, TN (US); Lesli Wilson, Springfield, IL (US); Scott Mueller, Litchfield, IL (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 53 days.

(21) Appl. No.: 15/911,051

(22) Filed: Mar. 2, 2018

(51) Int. Cl.
G06F 3/0484 (2013.01)
G16H 20/00 (2018.01)
G16H 50/20 (2018.01)
G16H 10/60 (2018.01)

(52) U.S. Cl.
CPC ......... G06F 3/04842 (2013.01); G16H 10/60 (2018.01); G16H 20/00 (2018.01); G16H 50/20 (2018.01)

(58) Field of Classification Search
CPC .... G06F 3/04842; G16H 10/60; G16H 50/20; G16H 20/00
See application file for complete search history.

(56) References Cited

U.S. PATENT DOCUMENTS

| 2005/0246200 A1* | 11/2005 | Thomson | G06Q 10/10 705/2 |
| 2009/0265185 A1* | 10/2009 | Finn | G06F 19/328 705/3 |
| 2010/0131482 A1* | 5/2010 | Linthicum | G06F 19/00 707/706 |
| 2012/0101847 A1* | 4/2012 | Johnson | G06Q 10/00 705/3 |

(Continued)

OTHER PUBLICATIONS

"How To—Collapsibles/Accordion" (article) [online]. W3Schools, [online]. Dec. 1, 2016. [Retrieved on Mar. 4, 2019]. Retrieved from the Internet <URL: https://www.w3schools.com/howto/howto_js_accordion.asp>.*

(Continued)

*Primary Examiner* — John T Repsher, III
(74) *Attorney, Agent, or Firm* — Medley, Behrens & Lewis, LLC (57) ABSTRACT

An improved graphical user interface (GUI) for displaying patient health records is described herein. A computing device transmits a query to a server computing device executing an electronic health records application (EHR). The EHR retrieves a computer-readable file for a patient comprising a plurality of file records, the plurality of file records including a file record reflective of a patient encounter with a healthcare worker for a healthcare issue. The EHR transmits data which causes the computing device to present a GUI including a first portion comprising an identity of the healthcare issue and a second portion comprising a treatment plan for the healthcare issue, patient symptoms, and obser- (Continued)

vations made by the healthcare worker during the patient encounter. The first portion is oriented above the second portion such that the healthcare issue can be identified without scrolling through the GUI or refreshing the GUI.

20 Claims, 8 Drawing Sheets

(56) References Cited

U.S. PATENT DOCUMENTS

2013/0197940 A1* 8/2013 Garber ............... G16H 10/60
705/3
2015/0317436 A1* 11/2015 Kutty ............... G16H 10/20
705/3

OTHER PUBLICATIONS

"Allscripts Professional" (Brochure) [online]. Henry Schein, [online]. Mar. 19, 2013. [Retrieved on Mar. 4, 2019]. Retrieved from the Internet <URL: https://www.henryschein.com/us-en/images/medical/Pro01_Professional_EHRBrochure.pdf>.*

"AHLTA Electronic Health Record Redesign" (article) [online]. Parsons Institute for Information Mapping, [online]. Dec. 20, 2016. [Retrieved on Mar. 4, 2019]. Retrieved from the Internet <URL: http://piim.newschool.edu/development/AHLTA-electronic-health-record-redesign>.*

File | Define File at Dictionary.com. (article) [online]. Dictionary.com. Archived Mar. 18, 2016. Retreived on Jul. 10, 2019. http://www.dictionary.com/browse/file.*

* cited by examiner

COMPUTING SYSTEM FOR PRESENTING PATIENT HEALTH RECORDS IN A PROBLEM-CENTRIC MANNER

BACKGROUND

Electronic health record applications (EHRs) are applications utilized by healthcare enterprises to generate and maintain health records for patients. As a patient visits different healthcare organizations using different EHRs, his or her medical records become scattered across various EHRs. This leads to "silos" of health data for the patient that can be difficult to access. For instance, a patient may make an emergency room visit, and a hospital system that operates the emergency room may use a first EHR to generate and maintain electronic patient records. Sometime thereafter, the patient may visit an orthopedic surgery center, where the center utilizes a second EHR to generate and maintain electronic patient records. Conventionally, a healthcare worker at the orthopedic surgery center is unable to access the electronic records about the patient generated and stored by the first EHR. Instead, the healthcare worker must contact the hospital that operates the emergency room, whereupon the hospital will provide a summary of an electronic patient record of interest to the healthcare worker at the orthopedic surgery center (presuming that the patient consented to the sharing of the electronic patient record).

Conventionally, healthcare workers employ a documentation method known as a "SOAP note" in connection with constructing an electronic record for a patient during a patient encounter, and hence conventional EHRs are configured to present patient health records in a SOAP format. SOAP is an acronym for "subjective, objective, assessment, and plan." Accordingly, a SOAP note comprises a subjective component, an objective component, an assessment component, and a plan component in sequential order. The subjective component appears first in the SOAP note and includes a description of patient problems as experienced by the patient. For instance, the subjective component can include a description of pain experienced by the patient. The objective component appears second in the SOAP note and includes information that the healthcare worker observes or measures from the patient during the patient encounter. For instance, the objective component can include vital signs and measurements, such as patient blood pressure. The assessment component appears third in the SOAP note and refers to a diagnosis based on the subjective and objective components of the SOAP note. Finally, the plan component appears at the end of the SOAP note and includes steps to be taken to treat the patient based on the assessment.

While widely used among healthcare workers, the SOAP note has disadvantages when used as a documentation method in an EHR. When a healthcare worker reviews healthcare records of a patient, oftentimes he or she is most interested in the assessment component (i.e., a diagnosis) and/or the plan component of a health record. However, in the SOAP note format, the assessment component and the plan component are not at the beginning of the health record, rather, they are the third and fourth components of the healthcare record. Thus, in order to determine past diagnoses of the patient and/or treatment plans, the healthcare worker will often have to scroll down on a computing device displaying the patient health records and/or navigate to a new page on the computing device. This results in a waste of computing resources and can be a time-consuming and frustrating experience for the healthcare worker. Furthermore, the problem is compounded when a patient has extensive health records, as the healthcare worker must navigate through multiple SOAP note format health records.

SUMMARY

The following is a brief summary of subject matter that is described in greater detail herein. This summary is not intended to be limiting as to the scope of the claims.

Described herein are various technologies pertaining to presenting patient health records in a problem-centric manner. More specifically, the technologies described herein conserve computing resources by presenting patient health problems (e.g., a diagnosis of a healthcare issue) at the forefront of a patient health record. Thus, a healthcare worker can easily locate prior health problems of a patient without having to resort to multiple page refreshes and/or scrolling through a graphical user interface (GUI).

A client computing device (e.g., a mobile computing device operated by a healthcare worker employed by a healthcare enterprise) receives input indicative of a patient (e.g., a patient identifier) by way of a client electronic health record application (client EHR) that is being executed by a processer of the client computing device. The client computing device then transmits a query to a server computing device that is in network communication with the client computing device, where the query comprises the patient identifier. The server computing device executes an electronic health records application (EHR) that is configured to retrieve a computer-readable file for the patient based on the query. The EHR (as well as the computer-readable file) is accessible to client computing devices of plurality of healthcare enterprises—thus, the architecture of the computing system described herein is contrary to conventional architectures, where EHRs acts as silos (as described above). The computer-readable file for the patient comprises a plurality of records, where the plurality of records include a record reflective of a patient encounter with a healthcare worker for a healthcare issue. The data in the record comprises, in sequence, data that is indicative of symptoms of the patient communicated to the healthcare worker during the patient encounter, observations made by the healthcare worker with respect to the patient during the patient encounter, an identity of the healthcare issue (i.e., a diagnosis), and a treatment plan for the healthcare issue. The EHR then transmits at least a portion of the computer-readable file to the client computing device.

Responsive to receiving at least the portion of the computer-readable file, the client computing device presents a GUI for the client EHR on a display of the client computing device. The GUI comprises a first portion and a second portion. The first portion comprises the identity of the healthcare issue. The second portion comprises the treatment plan for the healthcare issue, the symptoms of the patient communicated to the healthcare worker during the patient encounter, and observations made by the healthcare worker with respect to the patient during the patient encounter. The first portion is oriented above the second portion within the GUI such that the healthcare worker can view the identity of the healthcare issue without having to scroll down through the GUI and/or refresh the GUI.

In an example, the computer-readable file can include a second record reflective of a second patient encounter with a second healthcare worker for a second healthcare issue. The GUI can then further include a third portion and a fourth portion. The third portion can comprise an identity of the second healthcare issue. The fourth portion can comprise a treatment plan for the second healthcare issue, second symptoms of the patient communicated to the second healthcare worker during the second patient encounter, and second observations made by the second healthcare worker with respect to the patient during the second patient encounter. The third portion can be oriented below the second portion within the GUI, and the fourth portion can be oriented below the third portion within the GUI.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to presenting patient health records in a problem-centric manner are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Figure 1:
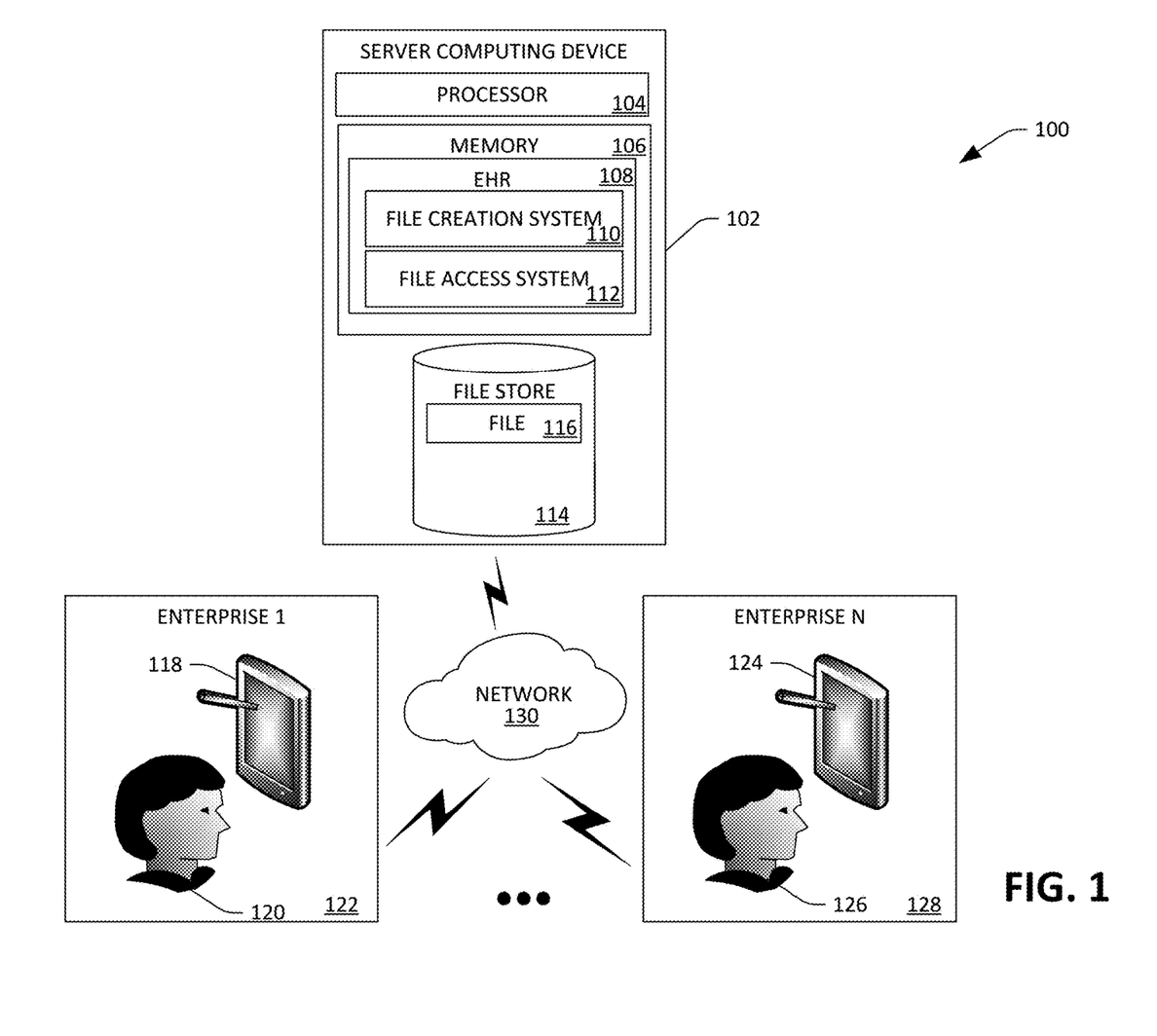
FIG. 1 is a functional block diagram of an exemplary computing system that facilitates presenting a patient problem-centric graphical user interface (GUI) on a display of a computing device.

With reference to FIG. 1, an exemplary computing system 100 that facilitates presenting a problem-centric graphical user interface (GUI) is illustrated. The computing system 100 can include a server computing device 102. The server computing device 102 includes a processor 104 and memory 106, wherein the memory 106 includes an electronic health records application (EHR) 108 loaded therein. Generally, the EHR 108 is configured to facilitate creation, storage, and maintenance of electronic health records for patients. As such, the EHR 108 comprises a file creation system 110 and a file access system 112. In general, the file creation system 110 is tasked with creating computer-readable files for patients. The file access system 112 is configured to ensure that data in the computer-readable files can only be accessed by healthcare workers who possess the requisite permission. The server computing device 102 additionally comprises a file store 114 that includes a computer-readable file 116 for a patient, wherein the EHR 108 has access to the file store 114. While the file store 114 is illustrated as including a single computer-readable file, it is understood that the file store 114 can include (separate) files for many different patients.

The computing system 100 may further include a first client computing device 118 (e.g., a mobile computing device, a desktop computing device, etc.) operated by a healthcare worker 120 in a first healthcare enterprise 122. In an example, the first healthcare enterprise 122 may be a or manage a hospital, an urgent care facility, a family doctor facility, etc. The first client computing device 118 is in communication with the server computing device 102 by way of a network 130 (e.g., the Internet). The first client computing device 118 is employed by the healthcare worker 120 to access the EHR 108. For instance, the first client computing device 118 may have a client EHR application installed thereon that interfaces with the EHR 108, wherein data can be transmitted between the client EHR and the EHR 108 to: 1) create and/or modify health records for a patient; and/or 2) retrieve information (e.g., records within files, etc.) from the file store 114. For example, the healthcare worker 120 can utilize the first client computing device 118 to set forth notes pertaining to a patient encounter, and the notes can be transmitted to the server computing device 102, wherein the EHR 108 can incorporate the notes into the computer-readable file 116.

The computing system 100 may also include an nth client computing device 124 operated by a second healthcare worker 126 employed by an nth healthcare enterprise 128. In an example, the nth enterprise 128 may be or manage a hospital, an urgent care facility, a family doctor facility, etc. The nth client computing device 124 is in communication with the server computing device 102 by way of the network 130. The nth client computing device 124 is employed by the second healthcare worker 126 to access the EHR 108. For instance, the nth client computing device 124 may have a client EHR application installed thereon that interfaces with the EHR 108, wherein data can be transmitted between the client EHR and the EHR 108 to: 1) create and/or modify health records for a patient; and/or 2) retrieve health records from the file store 114. For example, the healthcare worker 126 can utilize the nth client computing device 124 to enter thermometer readings taken over a range of time, and the thermometer readings can be transmitted to the server computing device 102, wherein the EHR 108 can incorporate the thermometer readings into the computer-readable file 116.

While the computing system 100 is depicted as both client computing devices 118 and 124 having access to the EHR 108, there are other architectures contemplated. For example, the server computing device 102 (or a collection of server computing devices) can execute a separate instance of the EHR 108 for each enterprise—thus, the first client computing device 118 interfaces with a first instance of the EHR executing on the server computing device 102, while the nth client computing device 124 interfaces with an nth instance of the EHR executing on the server computing device 102. In an exemplary implementation, these instances of the EHR may be executed in different virtual machines. In other examples, the instances of the EHR can be executed separately without requiring different virtual machines. For purposes of ease of explanation, the client computing devices 118 and 124 will be described as accessing the EHR 108; it is to be understood, however, that in practice the client computing device 118 and 124 will access and interact with different instances of the EHR 108.

The computing system 100 depicted in FIG. 1 is architecturally distinct from conventional EHR systems, in that the EHR 108 is simultaneously accessible to client computing devices of multiple healthcare organizations. As will be discussed below, the EHR can construct a single file for each patient, wherein client computing devices of different healthcare organizations are able to access and update respective portions of the file. Thus, in an example, the first client computing device 118 can be employed by the healthcare worker 120 to causes the EHR 108 to create a compute-readable file for a patient who is provided care by the first healthcare worker 122. Later, the patient may seek treatment from the nth healthcare worker 126—the client computing device 124 can cause the EHR 108 to access the computer-readable file and update such file; therefore, the EHR 108 maintains a single file for the patient, despite the patient being provided with care at several different healthcare organizations (that are independent of one another). The EHR 108 constructs the file in such a way that access privileges can be enforced by the EHR 108: thus, for example, the EHR 108 may restrict access to the client computing device 124 operated by the nth healthcare worker 126 to only portions of the file for which the nth enterprise and/or the nth healthcare worker 126 are authorized to access (which is different from what the first enterprise and/or the first healthcare worker 120 are able to access).

Figure 2:
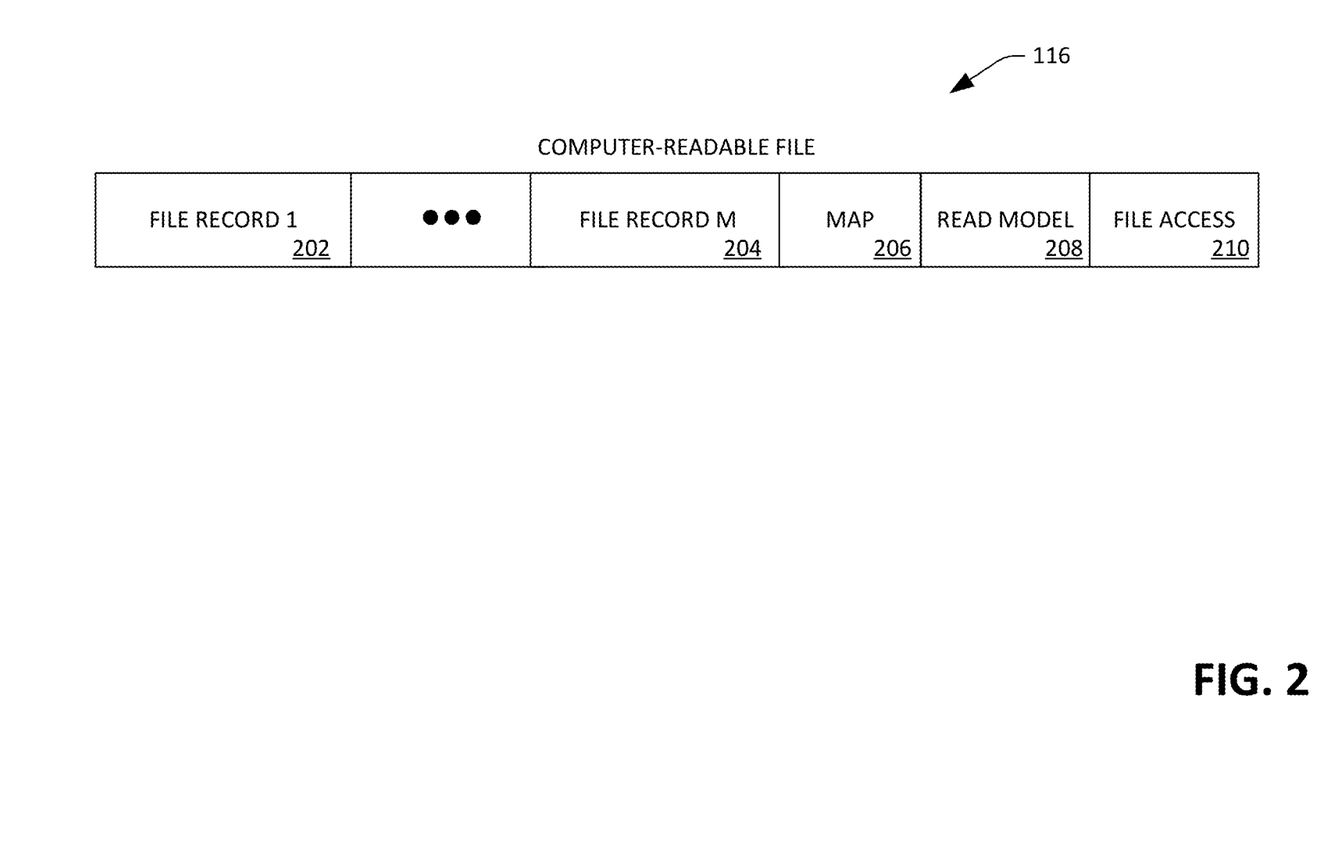
FIG. 2 is a schematic of an exemplary computer-readable file.

Referring now to FIG. 2, an exemplary schematic of the computer-readable file 116 is depicted. The computer-readable file 116 comprises a plurality of electronic records 202-204 that are appended to one another. The electronic records 202-204 are arranged in the computer-readable file 116 based upon when patient data was generated by the EHR 108. More specifically, the first electronic record 202 corresponds to first patient encounter data, while the mth electronic record 204 corresponds to mth patient encounter data that was created subsequent to the first patient encounter data. Therefore, the electronic records 202-204 are arranged in the computer-readable file 116 from oldest (at a beginning of the computer-readable file 116) to newest (at an end of the computer-readable file 116). Modification of the electronic records 202-204 is accomplished by identifying parent electronic records in the computer-readable file 116 for new data received by the server computing device 102, appending additional electronic records reflective of the new data to the computer-readable file 116, and updating pointer portions of the electronic records 202-204 to include pointers to the additional electronic records.

The computer-readable file 116 further comprises a map portion 206 that is appended to the mth (last) file record 204 in the computer-readable file 116. The map portion 206 identifies locations of the file records 202-204 in the computer-readable file 116. The computer-readable file 116 also comprises a read model 208 that is appended to the map portion 206. The EHR 108 can utilize the read model 208 to optimize retrieval of electronic records within the computer-readable file 116. Furthermore, the computer-readable file 116 can comprise a file access portion 210 appended to the read model 208. The file access portion 210 includes at least one attribute for at least one user that has permission to access the computer-readable file 116. For instance, the file access portion 210 can identify one or more enterprises, wherein employees in such enterprise(s) are able to access the file 116.

Figure 3:
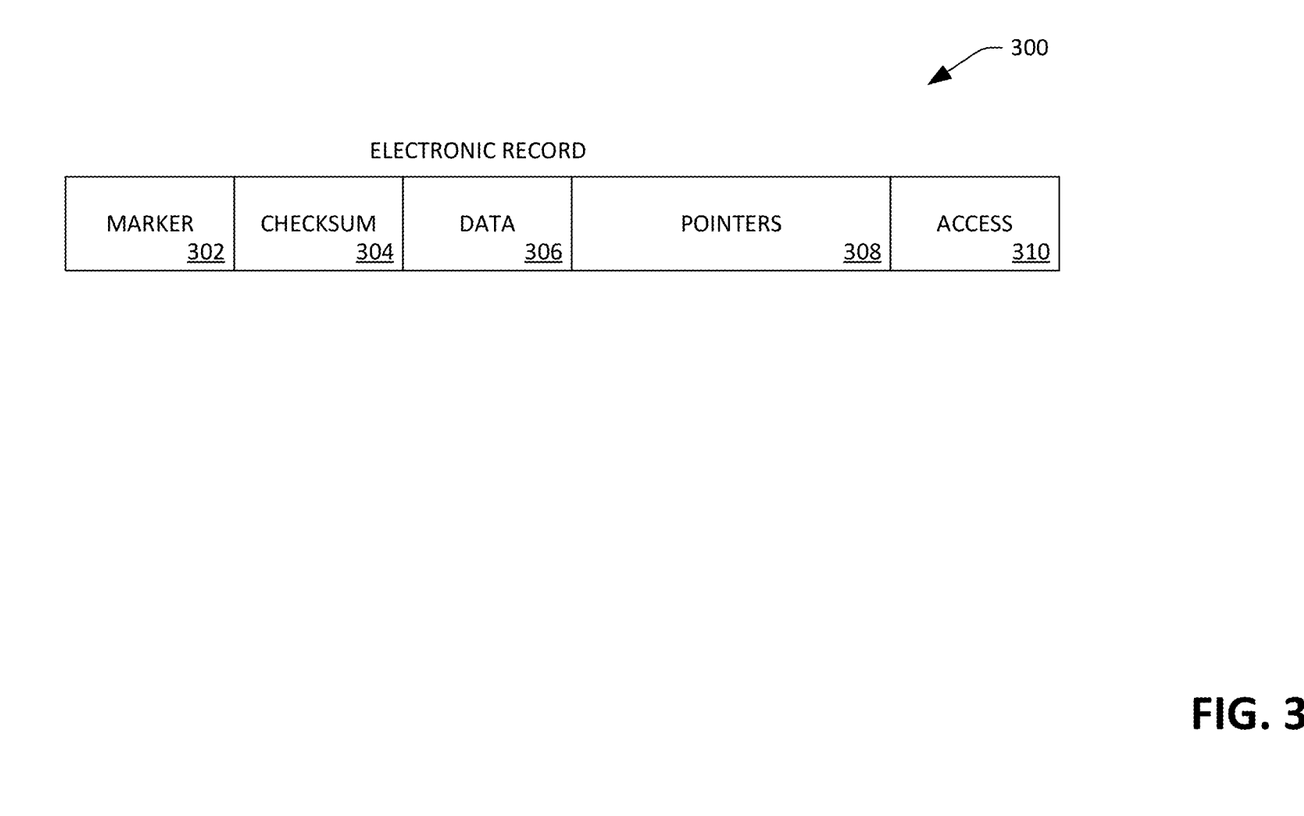
FIG. 3 is a schematic of an exemplary electronic record in a computer-readable file.

Turning now to FIG. 3, a schematic of an exemplary electronic record 300 that can be included in the computer-readable file 116 is illustrated. The electronic record 300 comprises data 306 about a patient encounter with a healthcare worker. The data about the patient can include an identity of a problem with respect to the patient being addressed by the healthcare worker, a treatment plan devices by the healthcare worker to address the problem, medications prescribed to the patient during the encounter, freehand notes set forth by the healthcare worker during the patient encounter, and so forth. The problem, medication, and the like can be assigned standardized codes, thereby ensuring consistent use of terminology across patient encounters (and thus across electronic records). This consistency in terminology allows for displaying medication information in a problem-centric manner, as problems are identified by standardized codes, and electronic records can be searched over for such standardized codes.

The electronic record 300 additionally comprises a pointer portion 308. The pointer portion 308 is an area reserved for pointers to child electronic records of the electronic record 300 within the computer-readable file 116. When the electronic record 300 is initially created and appended to the computer-readable file 116, the pointer portion 308 does not yet contain pointers. However, as additional electronic records related to the data 306 are added to the computer-readable file 116, the file creation system 110 can update the pointer portion 308 to include pointers to the additional electronic records.

The electronic record 300 may also comprise a checksum 304 for the electronic record 300, where the checksum is over at least the data 306. Generally, the checksum 304 is used when the computer-readable file 116 is read to ensure lack of corruption of the computer-readable file 116. Additionally, the checksum 306 can further be used to skip electronic records when the computer-readable file 116 is read by a computer-processor. The electronic record 300 also comprises a marker 302, wherein the marker 302 indicates a beginning of the electronic record 300.

Furthermore, the electronic record 300 comprises an access portion 310. The access portion 310 comprises one or more attributes of healthcare workers that have permission to access the data 306. In an embodiment, the attribute in the access portion 310 of the electronic record 300 can be an identifier for a healthcare worker. In another embodiment, the attribute in the access portion 310 of the file record 300 can be an identity of a healthcare enterprise (in which case any healthcare worker authenticated as belonging to the healthcare enterprise is authorized to access the data 306).

Returning to FIG. 1, exemplary operation of the computing system 100 is now set forth. It is contemplated that the first healthcare worker 120 belonging to the first healthcare organization 122 wishes to view health records for a patient. The first client computing device 118 may receive authentication data (e.g., username, password, biometric data, etc.) from the first healthcare worker 120, and the first client computing device 118 can transmit such authentication data to the server computing device 102, whereupon the EHR 108 authenticates the first healthcare worker 120. Thereafter, the first client computing device 118 receives input from the first healthcare worker 120 as to a patient by way of a client EHR that is being executed by the first client computing device 118. The client EHR can then transmit a query indicative of the input to the server computing device 102 (e.g., the query can include a patient identifier for the patient). The EHR 108 executing on the server computing device 102 can then execute a search over the data store 114 based on the query to retrieve the computer-readable file 116 for the patient. As discussed above, the computer-readable file 116 for the patient comprises a plurality of electronic records, with each electronic record in the plurality of electronic records representative of a patient encounter with a healthcare worker. Data in each electronic record comprises symptoms of the patient communicated by the patient to a healthcare worker during the patient encounter, observations made by the healthcare worker with respect to the patient during the patient encounter, an identity of the healthcare issue, and a treatment plan for the healthcare issue devised by the healthcare worker during the patient encounter. In an example, the order of such information can be identical for each electronic record. Responsive to retrieving the computer-readable file 116, the EHR 108 can transmit at least a portion of the computer-readable file 116 to the first client computing device 118 by way of the network 130. More specifically, the EHR 108 can transmit an electronic file record to the client computing device 118, wherein the first healthcare worker 120 is authorized to access the electronic file record of the computer-readable file 116.

The first client computing device 118 may then receive at least the portion of the computer-readable file 116 from the server computing device 102. Responsive to receiving at least the portion of the computer-readable file 116, the first client computing device 118 presents a GUI on a display of the first client computing device 118. The GUI comprises a first portion and a second portion. The first portion comprises the identity of the healthcare issue. The second portion comprises the treatment plan for the healthcare issue, the symptoms of the patient communicated by the patient to the healthcare worker 120 during the patient encounter, and observations made by the healthcare worker 120 with respect to the patient during the patient encounter. The first portion is oriented above the second portion such that the healthcare worker 120 can view the identity of the healthcare issue without having to scroll down through the GUI, refresh the GUI, or open a new window.

In an example, the plurality of electronic records may include a second electronic record that is representative of a second patient encounter with a healthcare worker for the healthcare issue, wherein the healthcare worker 120 is authorized to view content of the second electronic record. In such an example, the GUI can additionally include a third portion comprising a second treatment plan for the healthcare issue devised during the second patient encounter, second symptoms of the patient communicated by the patient during the patient encounter, and second observations made by the healthcare worker who provided care to the patient during the second patient encounter (where such healthcare worker can be the first healthcare worker 120 or other healthcare worker who provides care to the patient for the first enterprise 122). The third portion can be oriented below the second portion within the GUI.

In another example, the plurality of electronic records may also include a second electronic record that is representative of a second patient encounter with the nth healthcare worker 126 of the nth enterprise 128 for the healthcare issue. For example, the nth healthcare worker 126 can be a specialist that specializes in the healthcare issue. Thus, the GUI can further include a third portion comprising a second treatment plan for the healthcare issue devised by the nth healthcare worker 126 during the second patient encounter, second symptoms of the patient communicated by the patient to the nth healthcare worker 126, and second observations made by the nth healthcare worker 126 during the second patient encounter. The third portion can be oriented below the second portion within the GUI.

In yet another example, the plurality of electronic records may also include a second electronic record that is representative of a second patient encounter with the first healthcare worker 120 for a second healthcare issue. In this example, the GUI can further comprise a third portion and a fourth portion. The third portion can comprise an identity of the second healthcare issue. The fourth portion can comprise a second treatment plan for the second healthcare issue devised by the healthcare worker 120 (or another healthcare worker of the first enterprise 122) during the second patient encounter, second symptoms of the patient communicated by the patient to the first healthcare worker 120 during the second patient encounter, and second observations made by the first healthcare worker 120 with respect to the patient during the second patient encounter. The third portion can be oriented below the second portion within the GUI, and the fourth portion can be oriented below the third portion within the GUI.

In still yet another example, the plurality of electronic records may also include a second electronic record representative of a second patient encounter with the nth healthcare worker 126 of the nth enterprise 128 for a second healthcare issue. In this example, the GUI can further comprise a third portion and a fourth portion. The third portion can comprise an identity of the second healthcare issue. The fourth portion can comprise a second treatment plan for the second healthcare issue devised during the second patient encounter, second symptoms of the patient communicated by the patient to the nth healthcare worker 126 during the second patient encounter, and second observations made by the nth healthcare worker 126 with respect to the patient during the second patient encounter. The third portion can be oriented below the second portion within the GUI, and the fourth portion can be oriented below the third portion within the GUI.

As will be shown below, the GUI having the portions arranged as described above facilitates presentment of healthcare data in a problem-centric manner—thus, if the patient has a persistent healthcare issue, the GUI will present information (from multiple electronic records) in one place. This is contrary to the conventional approach, where electronic health data about the patient is shown with respect to time—the problem with this conventional approach is that the EHR may require the healthcare worker to scroll through information pertaining to many different patient encounters to identify all suitable patient encounters pertaining to the healthcare issue that is of interest to the healthcare worker.

Figure 4:
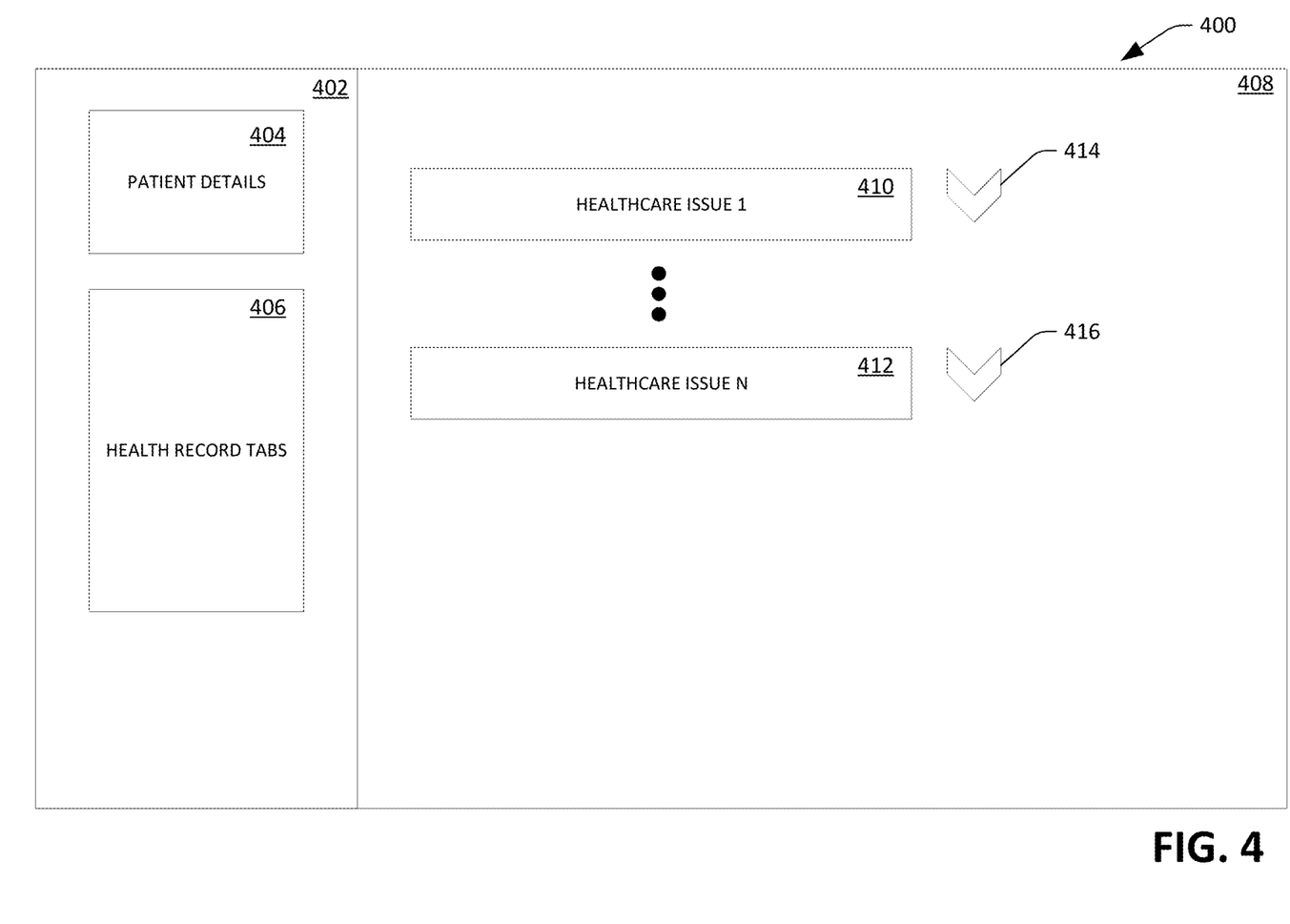
FIG. 4 depicts an exemplary GUI that presents patient health records in a problem-centric manner.

With reference to FIG. 4, an exemplary GUI 400 that facilitates presenting patient electronic health records in a problem-centric manner is depicted. The GUI 400 may comprise a sidebar 402. The sidebar 402 includes a patient details field 404 and a plurality of health records tabs 406. The patient details field 404 includes identifying information for a patient whose healthcare records are displayed on the GUI 400. For instance, the patient details field 404 can include a patient name, a patient date of birth and age, a patient sex, and a medical record number for the patient. The plurality of health records tab may include a tab for patient health history. When the tab for patient health history is selected, the GUI 400 can display identities of a plurality of healthcare issues of the patient 410-412. Each identity can include a corresponding selectable button 414-416. When a selectable button is selected within the GUI 400, additional information with respect to the healthcare issue (e.g., details of patient encounters for the healthcare issue) can be displayed within the GUI 400. Additionally or alternatively, each healthcare issue in the plurality of healthcare issues may be individually selectable within the GUI 400, and when a healthcare issue is selected, the additional information can be displayed within the GUI 400. Thus, unlike conventional EHR GUIs, a healthcare worker viewing the GUI 400 can quickly identify past healthcare issues of the patient with less screen refreshes and/or scrolling as compared to a conventional EHR GUI.

Figure 5:
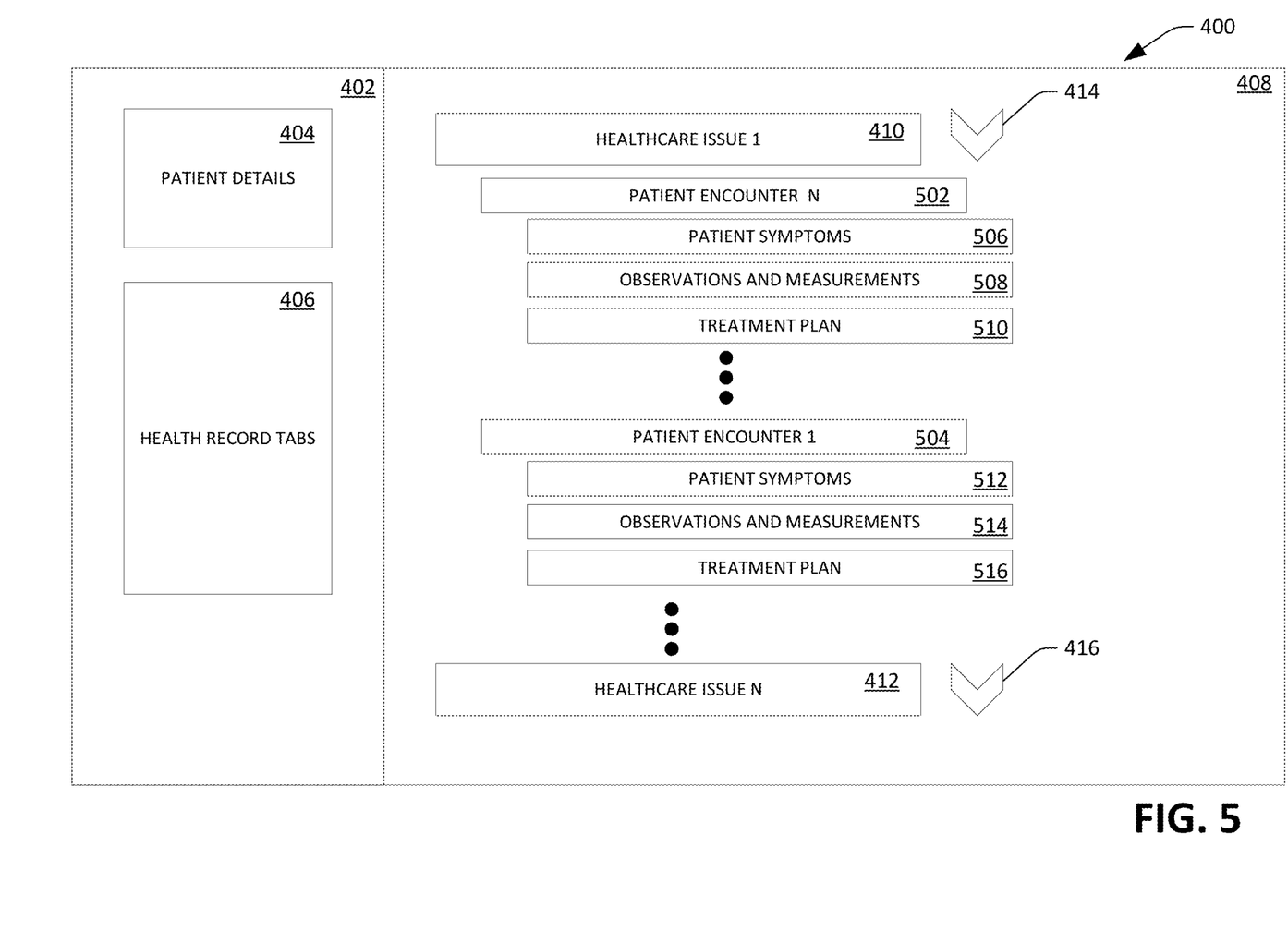
FIG. 5 illustrates a further exemplary GUI that presents patient health records in a problem-centric manner.

Turning now to FIG. 5, a further exemplary GUI 500 that facilitates presenting patient health records in a problem-centric manner is depicted. When the selectable button 414 for the first healthcare issue 410 is selected, information relating to each patient encounter for the first healthcare issue can be displayed within the GUI 400. In the embodiment shown in FIG. 5, a plurality of patient encounters 502-504 can be displayed within the GUI 400. It is contemplated the plurality of healthcare visits 502-504 will be sorted in reverse chronological order such that the most recent patient encounter (the nth healthcare visit 502) is oriented immediately below the identity of the healthcare issue 410 within the GUI 400; however, other orientations, such as chronological ordering, are possible. Each patient encounter includes symptoms of the patient 506, 512 communicated to the healthcare worker by the patient, observations 508, 514 made by the healthcare worker with respect to the patient during the patient encounter, and a treatment plan 510, 516 for the healthcare issue devised by the healthcare worker during the patient encounter.

The above-described technologies provide various advantages over conventional presentation of patient health records. By presenting patient problems (i.e., an identity of a healthcare issue) at a top portion of the GUI, computing resources may be conserved as less page refreshes are required to view patient health records. Furthermore, the technologies described above also reduce time spent by the healthcare worker in viewing patient health records, particularly when healthcare records of a patient are voluminous. As the GUI is organized based on patient problems (as opposed to the conventional SOAP note approach), details regarding multiple patient encounters for a healthcare issue can be presented within the GUI at the same time, thus enabling the healthcare worker to avoid looking though the entirety of the patient healthcare record when the healthcare worker is only interested in a particular healthcare issue.

Figure 6:
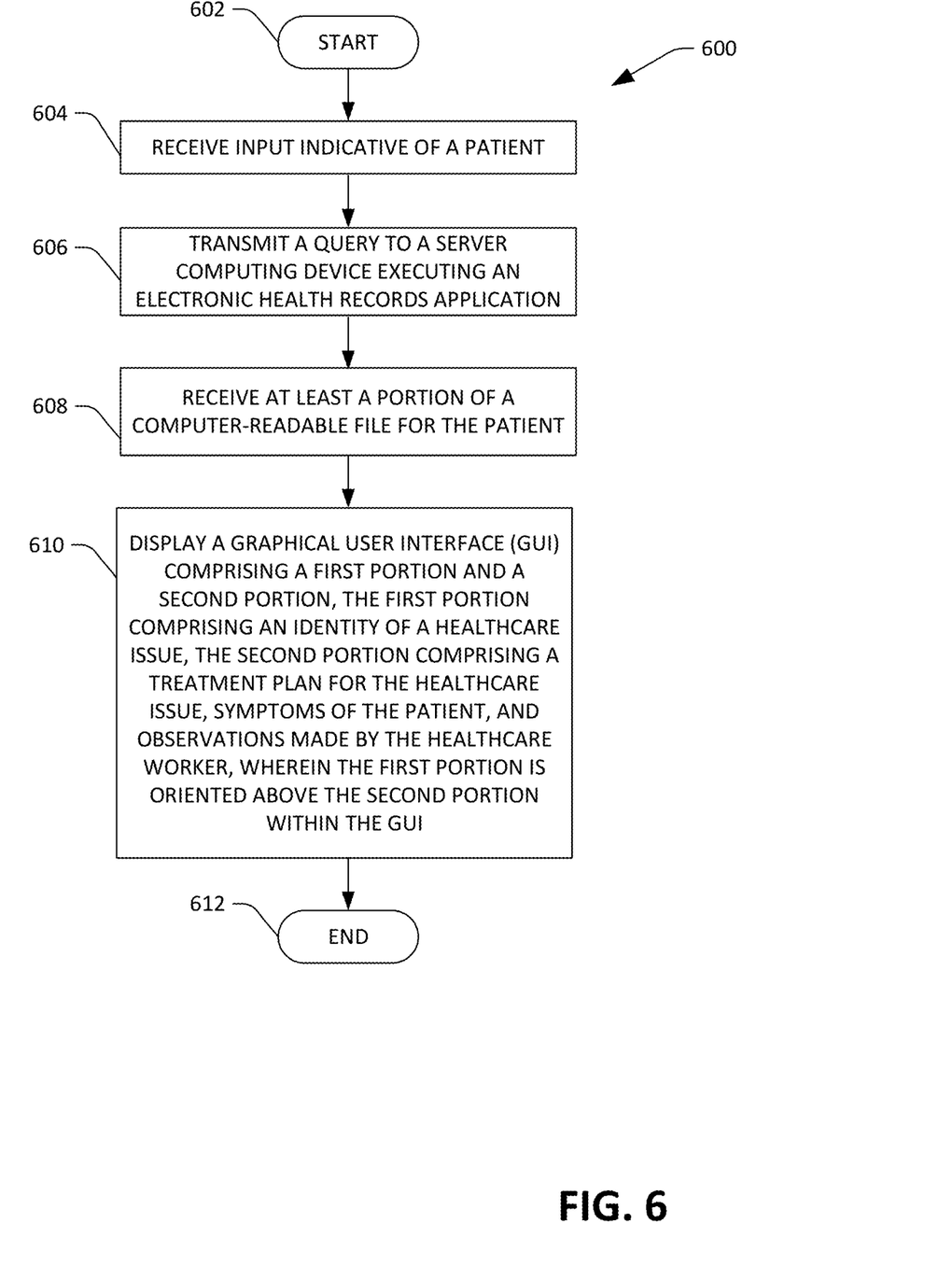
FIG. 6 is a flow diagram illustrating an exemplary methodology executed by a client computing device that facilitates presenting a patient problem-centric GUI on a display of the computing device.
Figure 7:
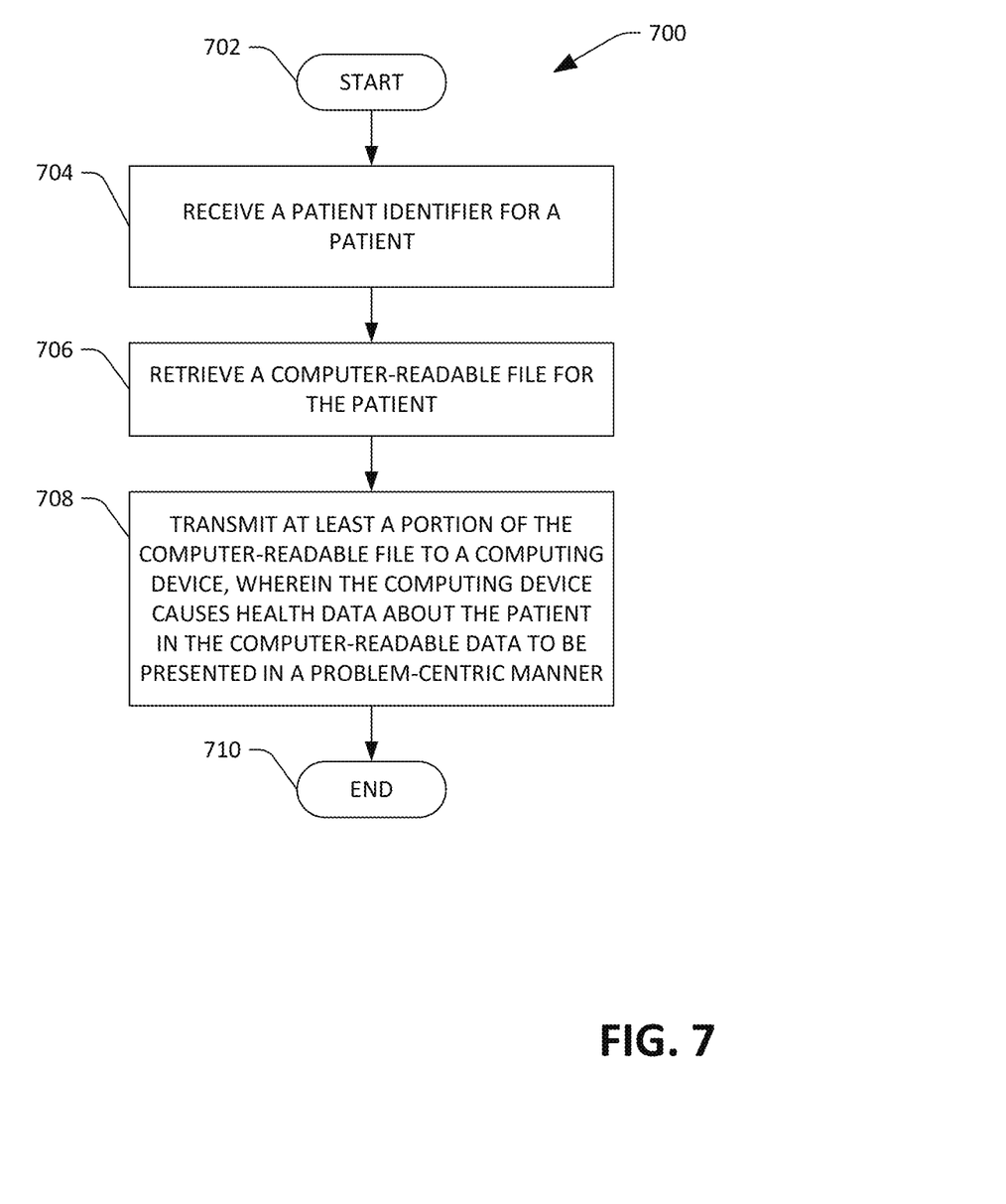
FIG. 7 is a flow diagram illustrating an exemplary methodology executed by a server computing device that facilitates presenting a patient problem-centric GUI on a display of a computing device.

FIGS. 6 and 7 illustrate exemplary methodologies relating to presenting patient healthcare records in a problem-centric manner. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 6, a methodology 600 performed at a computing device executing a client EHR that facilitates problem-centric display of patient health records within a GUI is illustrated. The methodology 600 begins at 602, and at 604 the computing device receives input indicative of a patient from a healthcare worker operating the computing device. At 606, responsive to receiving the input, the computing device transmits a query based on the input to a server computing device executing an EHR. The EHR is configured to retrieve a computer-readable file for a patient based on the query. The computer-readable file for the patient comprises a plurality of electronic records. The plurality of electronic records includes an electronic record that is representative of a patient encounter with a healthcare worker for a healthcare issue of the patient. The electronic record sequentially comprises symptoms of the patient communicated by the patient to the healthcare worker during the patient encounter, observations made by the healthcare worker with respect to the patient during the patient encounter, an identity of the healthcare issue, and a treatment plan for the healthcare issue.

At 608, the computing device receives at least a portion of the computer-readable file for the patient from the EHR. At 610, responsive to receiving at least the portion of the computer-readable file, the computing device presents a GUI for the client EHR on a display of the computing device. The GUI comprises a first portion and a second portion. The first portion comprises the identity of the healthcare issue. The second portion comprises the treatment plan for the healthcare issue, the symptoms of the patient communicated to the healthcare worker during the patient encounter, and the observations made by the healthcare worker with respect to the patient during the patient encounter. The first portion is oriented above the second portion within the GUI. The methodology 600 concludes at 612.

Turning now to FIG. 7, a methodology 700 executed by a server computing device that facilitates problem-centric display of patient health records is illustrated. The methodology 700 begins at 702, and at 704 the server computing executing an EHR receives a patient identifier for a patient from a computing device executing a client EHR. At 706, responsive to receiving the patient identifier, the EHR retrieves a computer-readable file for the patient by executing a search over a data store comprising a plurality of computer-readable files for a plurality of patients. The search is based on the patient identifier. At 708, the EHR transmits at least a portion of the computer-readable file for the patient to the computing device, wherein the computing device presents a GUI thereon as described above. The methodology 700 concludes at 710.

Figure 8:
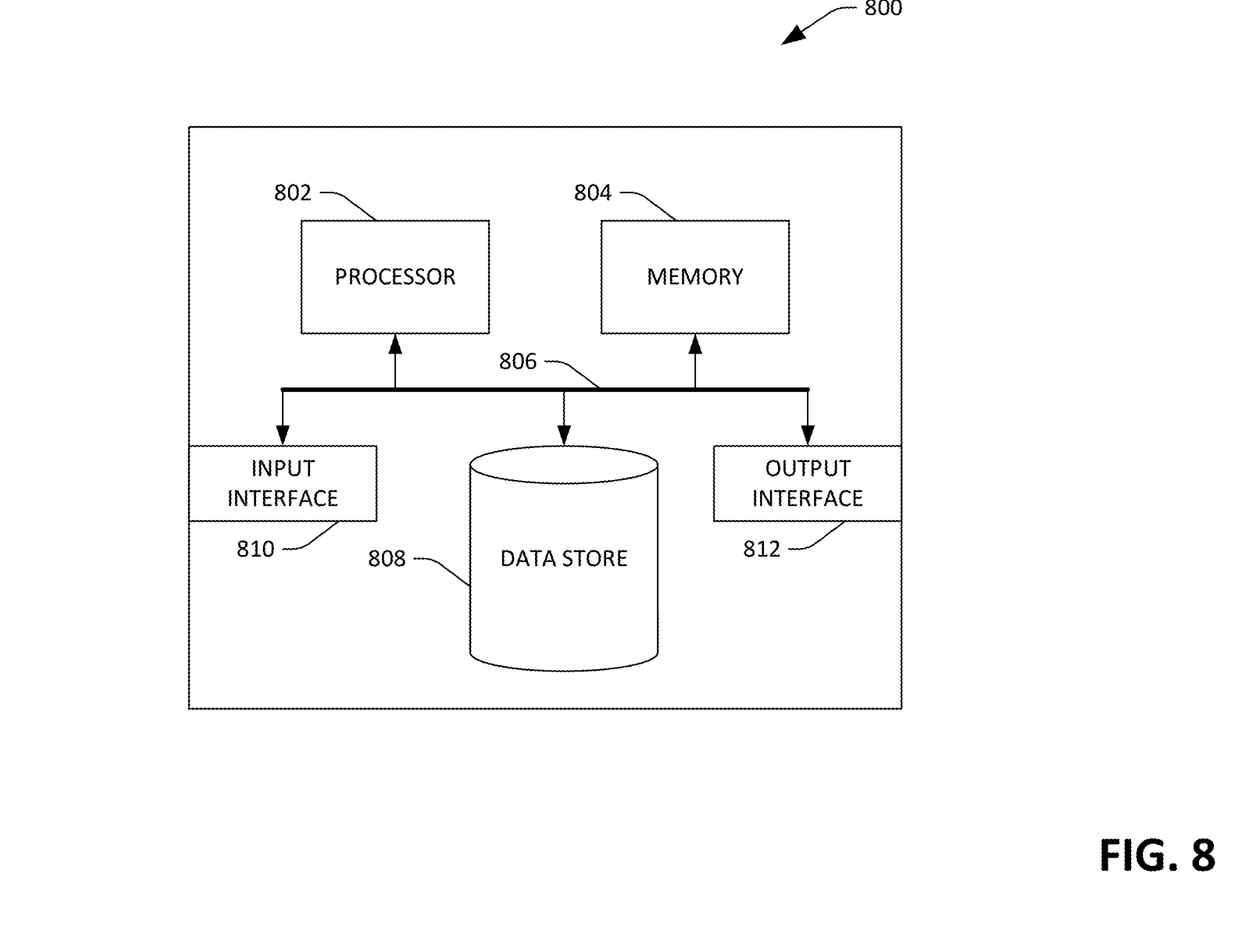
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that that presents patient health records to a healthcare worker. By way of another example, the computing device 800 can be used in a system that presents a GUI on a display of the computing device, wherein the GUI presents patients health records in a problem-centric manner. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store computer-readable files for patients.

The computing device 800 additionally includes a data store 808 that is accessible by the processor 802 by way of the system bus 806. The data store 808 may include executable instructions, computer-readable files for patients, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A computing device comprising:
    a processor;
    a display; and
    memory that stores instructions that, when executed by the processor, cause the processor to perform acts comprising:
        responsive to receiving input by way of a client electronic health records application (client EHR) that is being executed by the processor, the input indicative of a patient, transmitting a query to a server computing device that is in network communication with the computing device, wherein the server computing device executes an electronic health records application (EHR) that is accessible by computing devices of multiple healthcare enterprises, and further wherein the EHR is configured to retrieve a single computer-readable file for the patient based upon the query, wherein the single computer-readable file includes only data for the patient, the single computer-readable file for the patient comprising a plurality of electronic records generated by the computing devices of the multiple healthcare enterprises, each electronic record in the plurality of electronic records is appended to another electronic record within the single computer-readable file such that the plurality of electronic records are arranged chronologically within the single file, the plurality of electronic records including an electronic record that is representative of a patient encounter with a healthcare worker for a healthcare issue, the electronic record comprising:

symptoms of the patient communicated to the healthcare worker by the patient during the patient encounter;

observations made by the healthcare worker with respect to the patient during the patient encounter;

an identity of the healthcare issue that is a problem to the patient; and a treatment plan for the healthcare issue devised during the patient encounter, wherein the identity of the healthcare issue is assigned a standardized code within the single computer-readable file;

responsive to transmitting the query, receiving at least a portion of the single computer-readable file from the server computing device; and presenting a graphical user interface (GUI) of the client EHR on the display, the GUI comprising a first portion and a second portion, the first portion comprising the identity of the healthcare issue, the second portion comprising the treatment plan for the healthcare issue devised by the healthcare worker during the patient encounter, the symptoms of the patient communicated to the healthcare worker by the patient during the patient encounter, and the observations made by the healthcare worker with respect to the patient during the patient encounter, wherein the first portion is oriented above the second portion within the GUI.

2. The computing device of claim 1, wherein the GUI further comprises a selectable button oriented adjacent to the identity of the healthcare issue, the acts further comprising:
receiving a selection of the selectable button; and
responsive to receiving the selection of the selectable button, removing the second portion from the GUI.

3. The computing device of claim 2, the acts further comprising:
receiving a second selection of the selectable button; and
responsive to receiving the second selection of the selectable button, displaying the second portion within the GUI below the first portion.

4. The computing device of claim 1, wherein the plurality of electronic records includes a second electronic record that is representative of a second patient encounter with a second healthcare worker for the healthcare issue, the GUI further comprising a third portion, the third portion comprising a second treatment plan for the healthcare issue devised by the second healthcare worker during the second patient encounter, second symptoms of the patient communicated to the second healthcare worker by the patient during the second patient encounter, and second observations made by the second healthcare worker with respect to the patient during the second patient encounter, wherein the third portion is oriented below the second portion within the GUI.

5. The computing device of claim 1, wherein the plurality of electronic records includes a second electronic record that is representative of a second patient encounter with a second healthcare worker for a second healthcare issue, the GUI further comprising a third portion and a fourth portion, the third portion comprising an identity of the second healthcare issue, the fourth portion comprising a second treatment plan for the second healthcare issue devised by the second healthcare worker during the second patient encounter, second symptoms of the patient communicated to the second healthcare worker by the patient during the second patient encounter, and second observations made by the second healthcare worker with respect to the patient during the second patient encounter, wherein the third portion is oriented below the second portion within the GUI, wherein the fourth portion is oriented below the third portion within the GUI.

6. The computing device of claim 1, wherein the plurality of electronic records includes a second electronic record that is representative of a second patient encounter with a second healthcare worker for a second healthcare issue, the acts further comprising:
displaying the identity of the healthcare issue and an identity of the second healthcare issue within the GUI.

7. The computing device of claim 6, wherein the healthcare worker and the second healthcare worker are employed by a same healthcare enterprise.

8. The computing device of claim 6, wherein the healthcare worker is employed by a healthcare enterprise, and wherein the second healthcare worker is employed by a second healthcare enterprise.

9. The computing device of claim 1, wherein the computing device is a mobile computing device.

10. A method executed by a computing device, the method comprising:
receiving input from a healthcare worker by way of a client electronic health records application (client EHR) that is being executed on the computing device, the input indicative of a patient;
responsive to receiving the input, transmitting a query to a server computing device executing an electronic health records application (EHR) that is accessible by computing devices of multiple healthcare enterprises, wherein the EHR is configured to retrieve a single computer-readable file for the patient based upon the query, wherein the single computer-readable file includes only data for the patient, the single computer-readable file for the patient comprising a plurality of electronic records generated by the computing devices of the multiple healthcare enterprises, each electronic record in the plurality of electronic records is appended to another electronic record within the single computer-readable file such that the plurality of electronic records are arranged chronologically within the single file, the plurality of electronic records including an electronic record that is representative of a patient encounter with a healthcare worker for a healthcare issue, wherein the electronic record comprises, in sequence:
symptoms of the patient communicated to the healthcare worker by the patient during the patient encounter;

observations made by the healthcare worker with respect to the patient during the patient encounter;

an identity of the healthcare issue that is a problem to the patient; and a treatment plan for the healthcare issue devised during the patient encounter, wherein the identity of the healthcare issue is assigned a standardized code within the single computer-readable file; and presenting a graphical user interface (GUI) of the client EHR on the display, the GUI comprising a first portion and a second portion, the first portion comprising the identity of the healthcare issue, the second portion comprising the treatment plan for the healthcare issue, the symptoms of the patient communicated to the healthcare worker by the patient during the patient encounter, and the observations made by the healthcare worker with respect to the patient during the patient encounter, wherein the first portion is oriented above the second portion within the GUI.

11. The method of claim 10, wherein the computing device is a mobile computing device.

12. The method of claim 10, wherein the GUI further comprises a selectable button oriented adjacent to the identity of the healthcare issue, the acts further comprising:

receiving a selection of the selectable button; and responsive to receiving the selection of the selectable button, removing the second portion from the GUI.

13. The method of claim 10, wherein the plurality of electronic records includes a second electronic record that is representative of a second patient encounter with the healthcare worker for the healthcare issue, the GUI further comprising a third portion, the third portion comprising a second treatment plan for the healthcare issue devised during the second patient encounter, second symptoms of the patient communicated to the healthcare worker by the patient during the second patient encounter, and second observations made by the healthcare worker with respect to the patient during the second patient encounter, wherein the third portion is oriented below the second portion within the GUI.

14. The method of claim 10, wherein the plurality of electronic records includes a second electronic record that is representative of a second patient encounter with a second healthcare worker for a second healthcare issue, the GUI further comprising a third portion and a fourth portion, the third portion comprising an identity of the second healthcare issue, the fourth portion comprising a second treatment plan for the second healthcare issue devised during the second patient encounter, second symptoms of the patient communicated to the second healthcare worker by the patient during the second patient encounter, and second observations made by the second healthcare worker with respect to the patient during the second patient encounter, wherein the third portion is oriented below the second portion within the GUI, wherein the fourth portion is oriented below the third portion within the GUI.

15. A computer-readable storage medium comprising instruction that, when executed by a processor of a computing device, cause the processor to perform acts comprising:

responsive to receiving input by way of a client electronic health records application (client EHR) that is being executed by the processor, the input indicative of a patient, transmitting a query to a server computing device executing an electronic health records application (EHR) that is accessible by computing devices of multiple healthcare enterprises, wherein the EHR is configured to retrieve a single computer-readable file for the patient based on the query, wherein the single computer-readable file includes only data for the patient, the single computer-readable file for the patient comprising a plurality of electronic records generated by the computing devices of the multiple healthcare enterprises, each electronic record in the plurality of electronic records is appended to another electronic record within the single computer-readable file such that the plurality of electronic records are arranged chronologically within the single file, the plurality of electronic records including an electronic record that is representative of a patient encounter with a healthcare worker for a healthcare issue and a second electronic record that is representative of a second patient encounter with a second healthcare worker for a second healthcare issue, the electronic record comprising:

symptoms of the patient communicated to the healthcare worker by the patient during the patient encounter;

observations made by the healthcare worker with respect to the patient during the patient encounter;

an identity of the healthcare issue that is a problem to the patient; and a treatment plan for the healthcare issue devised during the patient encounter, wherein the identity of the healthcare issue is assigned a standardized code within the single computer-readable file;

displaying a graphical user interface (GUI) of the client EHR on the display, the GUI comprising a first portion and a second portion, the first portion comprising the identity of the healthcare issue, the second portion comprising an identity of the second healthcare issue, wherein the first portion is oriented above the second portion within the GUI;

receiving a selection of the first portion within the GUI; and responsive to receiving the selection of the first portion, updating the GUI to include a third portion, the third portion comprising the treatment plan for the healthcare issue devised during the patient encounter, the symptoms of the patient communicated to the healthcare worker by the patient during the patient encounter, and the observations made by the healthcare worker with respect to the patient during the patient encounter, wherein the third portion is oriented below the first portion within the GUI, wherein the third portion is oriented above the second portion within the GUI.

16. The computer-readable storage medium of claim 15, wherein the second electronic record comprises:

second symptoms of the patient communicated to the second healthcare worker by the patient during the patient encounter;

second observations made by the second healthcare worker with respect to the patient during the second patient encounter;

an identity of the second healthcare issue; and a second treatment plan for the second healthcare issue devised during the second patient encounter, wherein the identity of the second healthcare issue is assigned a second standardized code within the single computer-readable file, the acts further comprising:

receiving a selection of the second portion within the GUI;

responsive to receiving the selection of the second portion, updating the GUI to include a fourth portion, the fourth portion comprising the second treatment plan for the second healthcare issue devised during the second patient encounter, the second symptoms of the patient communicated to the second healthcare worker by the patient during the second patient encounter, and the second observations made by the second healthcare worker with respect to the patient during the second patient encounter, wherein the fourth portion is oriented below the second portion within the GUI.

17. The computer-readable storage medium of claim 15, wherein the healthcare worker is employed by a healthcare enterprise, and wherein the second healthcare worker is employed by a second healthcare enterprise that is different from the healthcare enterprise.

18. The computing device of claim 1, wherein the single computer-readable file comprises a file access portion, the file access portion identifying healthcare workers that have permission to access the single computer-readable file.

19. The method of claim 10, wherein the single computer-readable file comprises a file access portion, the file access portion identifying healthcare workers that have permission to access the single computer-readable file.

20. The computing device of claim 1, wherein within the second portion comprised by the GUI of the client EHR that is oriented below the first portion comprised by the GUI of the client EHR, the symptoms of the patient communicated to the healthcare worker during the patient encounter are oriented above the observations made by the healthcare worker during the patient encounter, and further wherein the observations made by the healthcare worker during the patient encounter are oriented above the treatment plan for the healthcare worker devised during the patient encounter.

* * * * *